US009750243B2

(12) United States Patent
Di Modugno et al.

(10) Patent No.: US 9,750,243 B2
(45) Date of Patent: *Sep. 5, 2017

(54) AQUEOUS ADJUVANT CONCENTRATES WITH IMPROVED SPRAY DRIFT PROPERTIES

(71) Applicant: LAMBERTI SpA, Albizzate (Varese) (IT)

(72) Inventors: Rocco Di Modugno, Spring, TX (US); James Dean Reiss, West Dundee, IL (US); Bradley Eidem, Spring, TX (US); Valentina Langella, Milan (IT); Mauro Riccaboni, Legnano (IT); Giovanni Floridi, Novara (IT); Giuseppe Li Bassi, Gavirate (IT)

(73) Assignee: LAMBERTI SPA, Albizzate (VA) (IT)

( * ) Notice: Subject to any disclaimer, the term of this patent is extended or adjusted under 35 U.S.C. 154(b) by 388 days.

This patent is subject to a terminal disclaimer.

(21) Appl. No.: 14/616,407

(22) Filed: Feb. 6, 2015

(65) Prior Publication Data

US 2016/0227768 A1 Aug. 11, 2016

(51) Int. Cl.

| | |
|---|---|
| *A01N 25/02* | (2006.01) |
| *A01N 25/30* | (2006.01) |
| *A01N 57/20* | (2006.01) |
| *A01N 37/10* | (2006.01) |
| *A01N 25/24* | (2006.01) |
| *A01N 37/38* | (2006.01) |

(52) U.S. Cl.

CPC ............. *A01N 25/24* (2013.01); *A01N 25/02* (2013.01); *A01N 25/30* (2013.01); *A01N 37/10* (2013.01); *A01N 37/38* (2013.01); *A01N 57/20* (2013.01)

(58) Field of Classification Search

CPC ........ A01N 25/02; A01N 25/30; A01N 57/20; A01N 37/10

USPC .................................................. 504/127, 362

See application file for complete search history.

(56) References Cited

U.S. PATENT DOCUMENTS

| | | | |
|---|---|---|---|
| 4,272,414 | A | 6/1981 | Vandersall |
| 4,883,537 | A | 11/1989 | Burdick |
| 4,971,728 | A | 11/1990 | Vandersall |
| 5,898,072 | A | 4/1999 | Bostroem et al. |
| 6,322,726 | B1 | 11/2001 | Vandersall et al. |
| 6,364,926 | B1 | 4/2002 | Gryzik et al. |

FOREIGN PATENT DOCUMENTS

| | | | |
|---|---|---|---|
| CN | 104478586 | A * | 4/2015 |
| EP | 0413274 | B1 | 11/1995 |
| EP | 2606724 | A1 | 6/2013 |
| WO | 2010100039 | A2 | 9/2010 |

* cited by examiner

*Primary Examiner* — Janet Epps-Smith
*Assistant Examiner* — Courtney Brown
(74) *Attorney, Agent, or Firm* — Mossman, Kumar & Tyler, PC

(57) ABSTRACT

An aqueous adjuvant concentrate can be prepared using a formulation including: a. from about 15 to about 45% by weight of a potassium salt chosen among di-potassium phosphate, potassium sulfate, potassium nitrate, tri-potassium citrate, potassium salts of ethylenediaminetetraacetic acid and mixture thereof; b. from about 0.5 to about 6% by weight of at least one surfactant and c. from about 3 to about 9% by weight of a hydroxypropyl tamarind gum; wherein a, b, and c are dissolved into the aqueous adjuvant. The aqueous adjuvant can include other compounds such as ah herbicide.

7 Claims, No Drawings

AQUEOUS ADJUVANT CONCENTRATES WITH IMPROVED SPRAY DRIFT PROPERTIES

TECHNICAL FIELD

The invention relates to a stable aqueous adjuvant concentrate having improved spray drift properties comprising a hydroxypropyl tamarind gum, a potassium salt and a surfactant.

The invention further relates to stable sprayable diluted herbicidal formations containing said aqueous adjuvant concentrate and at least a herbicide.

BACKGROUND OF THE ART

Many known agrochemicals have shown to be more effective in combination than when applied individually.

Herbicides, and in particular glyphosate, are usually sprayed in combination with organic adjuvants (such as surfactants acting as wetting agents and stickers) and inorganic adjuvants (such as inorganic nitrogen or potassium containing fertilizers). The presence of the various adjuvants guarantees good phytoactivity and avoids detrimental and/or unpredictable effects due to local conditions (water hardness, soil quality, weather conditions, etc).

Various systems have been devised for convenient dosing of agrochemicals, such as herbicides, on field, crop area, plants etc., for example spray pumps which spray diluted agrochemical formulations (tank mix) from a opportune manifold onto the area of land or crop area, or more complex apparatus which are designed to dose concentrated agrochemical formulations into the pump and to mix them with water before being sprayed.

During the spraying of agrochemicals, it is necessary to add anti-drift agents (drift control agents) in order to prevent the formation of fine droplets, which could be carried beyond the area intended to be treated. Without the use of anti-drift agents, the spraying could be largely inefficient, first of all because there could be an inadequate treatment of the land and crop areas to be treated and secondly because the extraneous spray, if carried beyond the intended treatment zone, could be detrimental to other crops, land and water courses.

Typical drift control agents are synthetic or natural polymers such as polyacrylamides, polyethylene oxides, polyvinyl pyrrolidones, guar gum and guar gum derivatives. In particular in the agriculture industry, polyacrylamides and guar gum and its derivatives are the standard additives for spray drift control.

It is usual to combine the anti-drift agent in the agrochemical formulations diluted for the spray application (tank-mix). Alternatively the anti-drift agent is dissolved in either the water which is fed into the spray pumps or applied directly into the spray pumps, usually at or shortly after the mixing zone where the water is mixed with the herbicide, pesticide or aqueous fertilizer concentrate. It is important that the spray drift chemical is correctly dosed and well dissolved to ensure that extraneous spray is not formed through under dosing or through overdosing or the spray angle is too narrow resulting in uneven distribution of the agrochemical.

However, these procedures have the problem that polymers, such as polyacrylamides, guar and guar derivatives, can be difficult to activate in field situations and polymer powders take a long time to dissolve. This can lead to the formation of gel particles which can block in-line screens and nozzles, resulting in pressure buildup in the system and spotty spray patterns.

A good solution to this problem could be dissolving/dispersing an adequate amount of anti-drift agent directly in the agrochemical concentrates. However, it is really difficult to dissolve sufficient polymer in the concentrates without obtaining solution with an unacceptable or unmanageable viscosity and/or to obtain stable solutions to achieve adequate spray drift in all cases. Furthermore, the types of polymeric anti-drift agents will be limited to the few which are easily soluble in the compositions to give adequate spray drift properties.

It is well known in the art that it is possible to prepare stable suspensions/dispersions of polysaccharides in concentrated solutions of electrolytes, such as ammonium or alkali salts of sulfate, nitrate and phosphate. These suspensions/dispersions are described for example in U.S. Pat. No. 4,971,728, U.S. Pat. No. 4,272,414 and U.S. Pat. No. 6,322,726, but none of these patents describes an adjuvant composition containing also a high amount of surfactant(s).

Suspensions/dispersions of polysaccharides in solution of electrolytes and surfactants are described in U.S. Pat. No. 4,883,537, U.S. Pat. No. 5,898,072, EP 413274 and US 2011/0054042 and EP 2606724.

US 2011/0054042, for example, describes compositions containing ammonium sulfate at concentration around 25-30% by weight and HPG at a concentration around 2-6% by weight and an alkyl betaine in the presence of a suspending agent, typically fumed silica, and/or a water soluble organic solvents.

U.S. Pat. No. 6,364,926 describes concentrated liquid adjuvant compositions comprising, by weight of the composition: a) about 25% to about 35% of a nitrogen compound in the form of an ammonium salt; b) about 0.1% to about 5% of an ampholytic surfactant, c) about 0.1% to about 2.5% of a drift control agent/deposition aid (hydroxypropyl guar), and d) about 55% to about 75% of a carrier. In this adjuvant concentrate both fertilizers and surfactants are present, but the concentration of drift control agent is quite low and does not allow high dilutions of the concentrates.

However these suspensions/dispersions are metastable systems and require the addition of a suspending agent for stabilization.

Unfortunately suspending agents are usually thickeners, such as clays, fumed silica or polymeric thickening agents, which further increase the viscosity of the suspensions/dispersions, reducing on-field manageability of the adjuvant compositions.

Alternatively, particular and time consuming methods of dissolution were developed, as described in EP 2606724 which discloses an aqueous adjuvant concentrate with improved spray drift properties and method for its preparation comprising the steps of: i) dissolving from 15 to 30% by weight, on the weight of the final concentrate, of ammonium sulfate in water; ii) adding to the solution from 1 to 10% by weight, on the weight of the final concentrate, of anionic esters of alkyl polyglycosides; iii) dispersing in the solution from 2 to 10% by weight, on the weight of the final concentrate, of hydroxypropyl guar or hydroxypropyl guar acetate; iiii) adding ammonium sulfate to the dispersion to reach an ammonium sulfate final concentration comprised between 33 and 40% by weight.

We have now discovered that stable and low viscosity aqueous adjuvant concentrates comprising, dissolved therein, up to 9% by weight of a hydroxypropyl tamarind gum (HPT) as anti-drift agents, from 15 to 45% by weight of potassium salts and up to 6% by weight of surfactants can be easily prepared, also without the use of a suspending agent or complex method of preparation. These concentrates contain high amount of dissolved adjuvants and anti-drift agent, are stable also in difficult environmental conditions, and, at the same time, they are easily pourable and manageable. For these reasons, they can be used to prepare directly in locus diluted sprayable herbicidal formulations, in particular glyphosate based formulations, with excellent anti-drift characteristics.

SUMMARY OF THE INVENTION

In one embodiment, the present invention is an aqueous adjuvant concentrate comprising, dissolved therein: from 15 to 45% by weight, preferably from 20 to 35% by weight, of a potassium salt chosen among di-potassium phosphate, potassium sulfate, potassium nitrate, tri-potassium citrate, potassium salts of ethylenediaminetetraacetic acid (EDTA) and mixture thereof; from 0.5 to 6% by weight, preferably 1 to 4% by weight, of at least a surfactant and, from 3 to 9% by weight, preferably 4 to 8% by weight, of a hydroxypropyl tamarind gum (HPT).

It is a further object of the present invention a sprayable herbicidal formulation comprising from 0.01 to 5% by weight of at least one herbicide and said aqueous adjuvant concentrate in such an amount that the concentration of HPT in the formulation is comprised between 0.01 and 0.4% by weight.

DETAILED DESCRIPTION OF THE INVENTION

Suitable potassium salts of EDTA are the mono-potassium EDTA, di-potassium EDTA, tri-potassium EDTA and tetra-potassium EDTA. Di-potassium EDTA is particularly preferred.

In a preferred embodiment, said potassium salt is a mixture of di-potassium phosphate, potassium nitrate and tri-potassium citrate.

Typically the aqueous adjuvant concentrate of the invention comprise at least 30% by weight, preferably from 40 to 60% by weight, of water.

Anionic, cationic, non-ionic and ampholytic surfactants and mixtures thereof can be used as the surfactant b). Suitable surfactants are, for example, nonionic emulsifiers and dispersants, such as: polyalkoxylated, preferably polyethoxylated, saturated and unsaturated aliphatic alcohols, having 8 to 24 carbon atoms in the alkyl radical, which is derived from the corresponding fatty acids or from petrochemical products, and having 1 to 100, preferably 4 to 40, ethylene oxide units (EO); polyalkoxylated, preferably polyethoxylated, arylalkylphenols, such as, for example, tristyrylphenol having an average degree of ethoxylation of between 8 and 80, preferably from 16 to 40; polyalkoxylated, preferably polyethoxylated, alkylphenols having one or more alkyl radicals, such as, for example, nonylphenol or tri-sec-butylphenol, and a degree of ethoxylation of between 2 and 40, preferably from 4 to 20; polyalkoxylated, preferably polyethoxylated, hydroxy-fatty acids or glycerides of hydroxy-fatty acids, such as, for example, castor oil, having a degree of ethoxylation of between 10 and 80; sorbitan or sorbitol esters with fatty acids or polyalkoxylated, preferably polyethoxylated, sorbitan or sorbitol esters; polyalkoxylated, preferably polyethoxylated, amines; di- and tri-block copolymers, for example from alkylene oxides, for example from ethylene oxide and propylene oxide, having average molar masses between 200 and 8000 g/mol, preferably from 1000 to 4000 g/mol; alkylpolyglycosides or polyalkoxylated, preferably polyethoxylated, alkylpolyglycosides.

Preferred nonionic surfactants are polyethoxylated alcohols, preferably from renewable resources, such as ethoxylated (4-8 EO) $C_{12}$-$C_{14}$ natural alcohol; polyethoxylated triglycerides of hydroxy-fatty acids and polyethylene oxide/polypropylene oxide block copolymers.

Also suitable are anionic surfactants, for example: polyalkoxylated, preferably polyethoxylated, surfactants which are ionically modified, for example by conversion of the terminal free hydroxyl function of the alkylene oxide block into a sulfate or phosphate ester; alkali metal and alkaline earth metal salts of alkylarylsulfonic acids having a straight-chain or branched alkyl chain; alkali metal and alkaline earth metal salts of paraffin-sulfonic acids and chlorinated paraffin-sulfonic acids; polyelectrolytes, such as lignosulfonates, condensates of naphthalenesulfonate and formaldehyde, polystyrenesulfonate or sulfonated unsaturated or aromatic polymers; anionic esters of alkylpolyglycosides, such as those described in WO 2010/100039, for example alkylpolyglucoside sulfosuccinate or citrate; sulfosuccinates which are esterified once or twice with linear, or branched aliphatic, cycloaliphatic and/or aromatic alcohols, or sulfosuccinates which are esterified once or twice with (poly) alkylene oxide adducts of alcohols.

Examples of cationic and ampholytic surfactants are quaternary ammonium salts, alkyl amino acids, and betaine or imidazoline amphotensides.

Preferably the surfactants are anionic surfactants. Preferred anionic surfactants are, for example, salts of alkyl sulfosuccinic acids, such as sodium dioctyl sulfosuccinate, and anionic esters of alkylpolyglycosides, in particular alkylpolyglucoside citrate.

Tamarind (*Tamarindus Indica*) is a leguminous evergreen tall tree produced in the tropics. Tamarind gum (tamarind powder or tamarind kernel powder), a xyloglucan polysaccharide, is obtained by extracting and purifying the seed powders, obtained by grinding the seeds of tamarind.

The polysaccharide molecule of the tamarind gum consists of a main linear chain of poly-glucose bearing xylose and galactoxylose substituents.

The procedure for the preparation of a hydroxypropyl tamarind gum is known in the art, and usually comprises the following steps: tamarind gum is treated with an organic-aqueous alkaline hydroxide and is reacted with propylene oxide; the alkaline hydroxide is neutralized, the possible organic diluent is distilled off and the product obtained is dried, ground and sieved to obtain a hydroxypropyl tamarind gum derivative.

The hydroxypropyl tamarind gum of the invention has preferably a molar hydroxypropyl substitution ranging from 0.1 to 2.5, preferably from 0.2 to 1.0.

The HP tamarind gum may also contain further substituent groups such as carboxyalkyl substituents, wherein the alkyl represents hydrocarbon moiety having 1 to 3 carbon atoms (e.g., carboxymethyl or carboxyethyl) or hydrophobic substituents or combination thereof.

The hydrophobic modification of the HP tamarind gum of the invention is obtained by the introduction of hydrophobic group.

Typical derivatizing agents bringing a hydrophobic group include $C_2$-$C_{24}$ linear or branched alkyl and alkenyl halides or linear, $C_6$-$C_{24}$ linear or branched alkyl and alkenyl epoxides and alkyl and alkenyl glycidyl ethers containing a $C_4$-$C_{24}$ linear or branched hydrocarbon group.

The hydrophobically modified HP tamarind gum of the invention may have hydrophobic degree of substitution ($DS_H$) of from $1*10^{-5}$ to $5*10^{-1}$, preferably from $1*10^{-4}$ to $1*10^{-1}$.

Preferably, the hydrophobically modified HP tamarind gum of the invention contains as hydrophobic groups $C_4$-$C_{24}$ alkyl chains.

Preferably the hydrophobizing agent is a alkyl or alkenyl glycidylether containing a $C_4$-$C_{24}$ linear or branched hydrocarbon group.

Halo-carboxylic acids, such as monochloroacetic acid, or their salts can be used for the preparation of carboxyalkyl HP tamarind gum.

The carboxyalkyl HP tamarind gum may have a carboxyalkyl DS of from 0.01 to 0.5, preferably from 0.05 to 0.3.

After the preparation, the HP tamarind gum can be treated with several known reagents, for example: caustic; acids; biochemical oxidants, such as galactose oxidase; chemical oxidants, such as hydrogen peroxide; and enzymatic reagents; or by physical methods using high speed agitation machines; thermal methods; and combinations of these reagents and methods. Reagents such as sodium metabisulfite or inorganic salts of bisulfite may also be optionally included.

The treatments described here above can be also performed on the tamarind gum before the derivatization process.

In a preferred embodiment, the HP tamarind gum is a depolymerized HP tamarind gum, which has been depolymerized by using chemicals, such as hydrogen peroxide, or cellulase enzymes.

In a further embodiment, the HP tamarind of the invention is purified by extraction of the impurities with an aqueous or aqueous-organic solvent before a final drying step so as to remove the salts and by-products formed during the reaction.

However, technical grade HP tamarind gum (i.e. not purified from the reaction by-products) is also suitable for the scope of the invention.

Preferably, the HP tamarind gum useful for the present invention has Brookfield® RV viscosity at 20° C., 20 rpm and 5% in water comprised between 500 and 20,000 mPa·s, preferably between 2,000 and 10,000 mPa·s.

Other commonly used water conditioners can be present in the composition of the invention in an amount ranging from 0.1 to 17% wt.

Examples of water conditioners are ammonium containing compounds, such, ammonium sulfate, ammonium nitrate, ammonium hydrogen sulfate, ammonium chloride, ammonium carbonate, ammonium hydrogen carbonate, ammonium phosphate, diammonium hydrogen phosphate, ammonium dihydrogen monophosphate, ammonium sodium hydrogen phosphate, monocarbamide dihydrogensulphate and mixtures of these.

In one embodiment of the invention, the pH of the adjuvant concentrate is brought to value ranging from 6.5 to 8.5, preferably from 7.0 to 8.0, by adding an appropriate amount of acid.

Carboxylic acids, both mono- and poly-carboxylic acids, are the preferred acids. Suitable examples are, without limitation, acetic acid, propanoic acid, butanoic acid, gluconic acid, lactic acid, oxalic acid, succinic acid, pyruvic acid malic, acid, malonic acid, citric acid, isocitric acid and mixtures thereof.

In a further embodiment of the invention, the aqueous adjuvant concentrate comprises from 0.03 to 1% by weight of a suspending agent. Any kind of suspending agent can be used for the realization of the present invention. Suitable suspending agents include, but are not limited to, silica, attapulgite and bentonite clays, or their derivatives such as hydrated fumed silica or amine treated attapulgite clays.

Optionally, the adjuvant concentrate may also include additives commonly used in the field, such as humectants, corrosion inhibitors, microbial inhibitors, anti-foam agents, or mixture thereof.

No special or particular equipment is required for the preparation of the aqueous adjuvant concentrate of the invention. The inorganic salt and the surfactant, and optionally other additives, can be dissolved in water utilizing a common equipment. The same equipment can be used for dissolving the tamarind gum derivatives in the obtained salt solution.

The aqueous adjuvant concentrate is stable; with the term "stable" we mean that no phase separation or precipitation or gelification occur, also in difficult environmental conditions, such as high (>40° C.) or low (<10° C.) temperatures for at least one week from its preparation.

The stability of the suspension of this invention can be further improved by mixing the dispersion under vacuum, so as to remove entrapped air.

Usually, the aqueous adjuvant concentrates of the invention have a Brookfield® RV viscosity, at 5 rpm and 20° C., comprised between 2000 and 8000 mPa·s.

The aqueous adjuvant concentrates of the invention are pourable, stable, and can be stored for a long time without settling or precipitation of solid components from the composition, despite the large amount of inorganic salts and surfactants that they contain; advantageously, they do not comprise any suspending agent or water soluble organic solvent, except the hydroxypropyl tamarind gum.

The sprayable herbicide formulations according to the invention are diluted and are obtained by adding the adjuvant concentrates to formulated herbicides, or vice-versa, and possibly diluting with water to the desired concentration in order to obtain aqueous formulation which can be directly sprayed on the fields.

Alternatively, the formulated herbicide and/or the adjuvant concentrates may be previously diluted and then mixed.

Preferably the HP tamarind gum of the invention is present in the diluted agrochemical spray formulation at a concentration ranging from 0.01 to 0.40% by weight.

The term "diluted" is used herein with reference to herbicide active content comprised between 0.001 and 20% by weight.

Said sprayable herbicide formulations comprise herbicidal active compounds, such as Acetochlor, Acibenzolar, Acibenzolar-S-methyl, Acifluorfen, Acifluorfen-sodium, Aclonifen, Alachlor, Allidochlor, Alloxydinn, Alloxydinn-sodium, Ametryn, Amicarbazone, Amidochlor, Amidosulfuron, Aminocyclopyrachlor, Aminopyralid, Amitrole, Ammonium sulfamat, Ancymidol, Anilofos, Asulam, Atrazine, Azafenidin, Azimsulfuron, Aziprotryn, Beflubutamid, Benazolin, Benazolin-ethyl, Bencarbazone, Benfluralin, Benfuresate, Bensulide, Bensulfuron, Bensulfuron-methyl, Bentazone, Benzfendizone, Benzobicyclon, Benzofenap, Benzofluor, Benzoylprop, Bicyclopyrone, Bifenox, Bispyribac, Bispyribac-sodium, Bromacil, Bromobutide, Bromofenoxim, Bromoxynil, Bromuron, Buminafos, Busoxinone, Butachlor, Butafenacil, Butamifos, Butenachlor, Butralin, Butroxydim, Butylate, Cafenstrole, Carbetamide, Carfentrazone, Carfentrazone-ethyl, Chlomethoxyfen, Chloramben, Chlorazifop, Chlorazifop-butyl, Chlorbromuron, Chlorbufam, Chlorfenac, Chlorfenac-sodium, Chlorfenprop, Chlorflurenol, Chlorflurenol-methyl, Chloridazon, Chlorimuron, Chlorimuron-ethyl, Chlormequat-chloride, Chlornitrofen, Chlorophthalim, Chlorthal-dimethyl, Chlorotoluron, Chlorsulfuron, Cinidon, Cinidon-ethyl, Cinmethylin, Cinosulfuron, Clethodim (C10), Clodinafop, Clodinafop-propargyl, Clofencet, Clomazone, Clomeprop, Cloprop, Clopyralid (C1), Cloransulam, Cloransulam-methyl, Cumyluron, Cyanamide, Cyanazine, Cyclanilide, Cycloate, Cyclosulfamuron, Cycloxydim (C11), Cycluron, Cyhalofop, Cyhalofop-butyl, Cyperquat, Cyprazine, Cyprazole, 2,4-D, 2,4-DB, Dalapon, Daminozide, Dazomet, n-Decanol, Desmedipham, Desmetryn, Detosyl-Pyrazolate (DTP), Diallate, Dicamba, Dichlobenil, Dichlorprop, Dichlorprop-P, Diclofop, Diclofop-methyl, Diclofop-P-methyl, Diclosulam, Diethatyl, Diethatyl-ethyl, Difenoxuron, Difenzoquat, Diflufenican, Diflufenzopyr, Diflufenzopyr-sodium, Dimefuron, Dikegulac-sodium, Dimefuron, Dimepiperate, Dimethachlor (C2), Dimethametryn, Dimethenamid, Dimethenamid-P, Dimethipin, Dimetrasulfuron, Dinitramine, Dinoseb, Dinoterb, Diphenamid, Dipropetryn, Diquat, Diquat-dibromide, Dithiopyr, Diuron, DNOC, Eglinazine-ethyl, Endothal, EPTC, Esprocarb, Ethalfluralin, Ethametsulfuron, Ethametsulfuron-methyl, Ethephon, Ethidimuron, Ethiozin, Ethofumesate, Ethoxyfen, Ethoxyfen-ethyl, Ethoxysulfuron, Etobenzanid, F-5331, d.h. N-[2-Chloro-4-fluoro-5-[4-(3-fluoropropyl)-4,5-dihydro-5-oxo-1H-tetrazol-1-yl]-phenyl]-ethan sulfonamide, F-7967, d.h. 3-[7-Chloro-5-fluoro-2-(trifluoromethyl)-1H-benzimidazol-4-yl]-1-methyl-6-(trifluormethyl)pyrimidin-2,4(1H,3H)-dione, Fenoprop, Fenoxaprop, Fenoxaprop-P, Fenoxaprop-ethyl, Fenoxaprop-P-ethyl (C3), Fenoxasulfone, Fentrazamide, Fenuron, Flamprop, Flamprop-M-isopropyl, Flamprop-M-methyl, Flazasulfuron, Florasulam, Fluazifop, Fluazifop-P, Fluazifop-butyl, Fluazifop-P-butyl, Fluazolate, Flucarbazone, Flucarbazone-sodium, Flucetosulfuron, Fluchloralin, Flufenacet (Thiafluamide), Flufenpyr, Flufenpyr-ethyl, Flumetralin, Flumetsulam, Flumiclorac, Flumiclorac-pentyl, Flumioxazin, Flumipropyn, Fluometuron, Fluorodifen, Fluoroglycofen, Fluoroglycofen-ethyl, Flupoxam, Flupropacil, Flupropanate, Flupyrsulfuron, Flupyrsulfuron-methyl-sodium, Flurenol, Flurenol-butyl, Fluridone, Flurochloridone, Fluroxypyr, Fluroxypyr-meptyl, Flurprimidol, Flurtamone, Fluthiacet, Fluthiacet-methyl, Fluthiamide, Fomesafen, Foramsulfuron, Forchlorfenuron, Fosamine, Furyloxyfen, Glufosinate, Glufosinate ammonium, Glyphosate, Glyphosate-diammonium, Glyphosate-isopropylammonium, Glyphosate-potassium, H-9201, d.h. 0-(2,4-Dimethyl-6-nitrophenyl)-O-ethyl-isopropyl phosphoramidothioate, Halosafen, Halosulfuron, Halosulfuron-methyl, Haloxyfop, Haloxyfop-p (C4), Haloxyfop-ethoxyethyl, Haloxyfop-P-ethoxyethyl, Haloxyfop-methyl, Haloxyfop-P-methyl, Hexazinone, HW-02, d.h. 1-(Dimethoxyphosphoryl)-ethyl(2,4-dichlorophenoxy)acetate, Imazamethabenz, Imazamethabenz-methyl, Imazamox (C9), Imazamox-ammonium, Imazapic, Imazapyr, Imazapyr-isopropylammonium, Imazaquin, Imazaquin-ammonium, Imazethapyr, Imazethapyr-ammonium, Imazosulfuron, Inabenfide, Indanofan, Indaziflam, Indolacetic acid (IAA), 4-Indol-3-yl-butirric acid (IBA), Iodosulfuron, Iodosulfuron-methyl-sodium, Ioxynil, Ipfencarbazone, Isocarbamid, Isopropalin, Isoproturon, Isouron, Isoxaben, Isoxachlortole, Isoxaflutole, Isoxapyrifop, KUH-043, d.h. 3-({[5-(Difluormethyl)-1-methyl-3-(trifluoromethyl)-1H-pyrazol-4-yl]methyl}sulfonyl)-5,5-dimethyl-4,5-dihydro-1,2-oxazole, Karbutilate, Ketospiradox, Lactofen, Lenacil, Linuron, MCPA, MCPB, MCPB-methyl, -ethyl and -sodium, Mecoprop, Mecoprop-sodium, Mecoprop-butotyl, Mecoprop-P-butotyl, Mecoprop-P-dimethylammoniunn, Mecoprop-P-2-ethylhexyl, Mecoprop-P-potassium, Mefenacet, Mefluidide, Mepiquat-chlorid, Mesosulfuron, Mesosulfuron-methyl, Mesosulfuron-methyl-Na, Mesotrione, Methabenzthiazuron, Metam, Metamifop, Metamitron, Metazachlor (C5), Metazasulfuron, Methazole, Methiopyrsulfuron, Methiozolin, Methoxyphenone, Methyldymron, 1-Methylcyclopropen, Methylisothiocyanat, Metobenzuron, Metobromuron, Metolachlor, S-Metolachlor, Metosulam, Metoxuron, Metribuzin, Metsulfuron, Metsulfuron-methyl, Molinate, Monalide, Monocarbamide, Monocarbamide-dihydrogensulfat, Monolinuron, Monosulfuron, Monosulfuron-ester, Monuron, MT-128, d. h. 6-Chloro-N-[(2E)-3-chloroprop-2-en-1-yl]-5-methyl-N-phenylpyridazin-3-amine, MT-5950, d.h. N-[3-Chloro-4-(1-methylethyl)-phenyl]-2-methylpentanamide, NGGC-011, Naproanilide, Napropamide (C6), Naptalam, NC-310, d.h.4-(2,4-Dichlorobenzoyl)-1-methyl-5-benzyloxypyrazole, Neburon, Nicosulfuron, Nipyraclofen, Nitralin, Nitrofen, Nitrophenolat-sodium (isomer mixture), Nitrofluorfen, Nonansaure, Norflurazon, Orbencarb, Orthosulfamuron, Oryzalin, Oxadiargyl, Oxadiazon, Oxasulfuron, Oxaziclomefone, Oxyfluorfen, Paclobutrazol, Paraquat, Paraquat-dichlorid, Pendimethalin, Pendralin, Penoxsulam, Pentanochlor, Pentoxazone, Perfluidone, Pethoxamid, Phenisopham, Phenmedipham, Phenmedipham-ethyl, Picloram, Picolinafen, Pinoxaden, Piperophos, Pirifenop, Pirifenop-butyl, Pretilachlor, Primisulfuron, Primisulfuron-methyl, Probenazole, Profluazol, Procyazine, Prodiamine, Prifluraline, Profoxydim, Prohexadione, Prohexadione-calcium, Prohydrojasmone, Prometon, Prometryn, Propachlor, Propanil, Propaquizafop, Propazine, Propham, Propisochlor, Propoxycarbazone, Propoxycarbazone-sodium, Propyrisulfuron, Propyzamide, Prosulfalin, Prosulfocarb, Prosulfuron, Prynachlor, Pyraclonil, Pyraflufen, Pyraflufen-ethyl, Pyrasulfotole, Pyrazolynate (Pyrazolate), Pyrazosulfuron, Pyrazosulfuron-ethyl, Pyrazoxyfen, Pyribambenz, Pyribambenz-isopropyl, Pyribambenz-propyl, Pyribenzoxim, Pyributicarb, Pyridafol, Pyridate (C7), Pyriftalid, Pyriminobac, Pyriminobac-methyl, Pyrimisulfan, Pyrithiobac, Pyrithiobac-sodium, Pyroxasulfone, Pyroxsulam, Quinclorac, Quinmerac, Quinoclamine, Quizalofop, Quizalofop-ethyl, Quizalofop-P, Quizalofop-P-ethyl, Quizalofop-P-tefuryl, Rimsulfuron, Saflufenacil, Secbumeton, Sethoxydim, Siduron, Simazine, Simetryn, SN-106279, d. h. Methyl-(2R)-2-({7-[2-chloro-4-(trifluoromethyl)phenoxy]-2-naphthyl}oxy) propanoate, Sulcotrione, Sulfallate (CDEC), Sulfentrazone, Sulfonneturon, Sulfonneturon-methyl, Sulfosate (Glyphosate-trimesium), Sulfosulfuron, SYN-523, SYP-249, d.h. 1-Ethoxy-3-methyl-1-oxobut-3-en-2-yl-5-[2-chloro-4-(trifluoromethyl)phenoxy]-2-nitrobenzoate, SYP-300, d.h.1-[7-Fluoro-3-oxo-4-(prop-2-in-1-yl)-3,4-dihydro-2H-1,4-benzoxazin-6-yl]-3-propyl-2-thioxoimidazolidin-4,5-dione, Tebutam, Tebuthiuron, Tecnazene, Tefuryltrione, Tembotrione, Tepraloxydim, Terbacil, Terbucarb, Terbuchlor, Terbumeton, Terbuthylazine, Terbutryn, Thenylchlor, Thiafluamide, Thiazafluron, Thiazopyr, Thidiazimin, Thidiazuron, Thiencarbazone, Thiencarbazone-methyl, Thifensulfuron, Thifensulfuron-methyl, Thiobencarb, Tiocarbazil, Topramezone, Tralkoxydim, Triallate, Triasulfuron, Triaziflam, Triazofenamide, Tribenuron, Tribenuron-methyl, Trichloroacetic acid (TCA), Triclopyr, Tridiphane, Trietazine, Trifloxysulfuron, Trifloxysulfuron-sodium, Trifluralin (C8), Triflusulfuron, Triflusulfuron-methyl, Trimeturon, Trinexapac, Trinexapac-ethyl, Tritosulfuron, Tsitodef, Uniconazole, Uniconazole-P, Vernolate, ZJ-0862, d.h.3,4-Dichloro-N-{2-[(4,6-dimethoxypyrimidin-2-yl)oxy]benzyl}aniline or mixture thereof.

The adjuvant concentrates of the present invention are particularly suited for the preparation of sprayable formulations of N-(phosphonomethyl) glycine (Glyphosate) and its salts, Dicamba and its salts and 2-4D and its salts, and mixture thereof. Particularly preferred are formulations comprising N-(phosphonomethyl) glycine and Dicamba, or salts thereof.

Other biologically active ingredients such as other pesticides, plant growth regulators, algicides, fungicides, bactericides, viricides, insecticides, acaricides and nematicides may be added as partners in the sprayable diluted herbicide formulations.

The sprayable herbicidal formulations of the invention may additionally comprise other conventional additives, including thickeners, flow enhancers, wetting agents, buffers, lubricants, fillers, deposition enhancers, evaporation retardants, frost protecting agents, insect attracting odor agents, UV protecting agents, fragrances, anti-foam agents and the like.

Application rates will depend upon the weeds to be controlled and the degree of control desired. In general, the herbicidal formulations of this invention are most efficiently employed at a rate of 0.001 to 22.4 kilograms per hectare of the active ingredients, preferably 0.01 to 16.8 kilograms per hectare.

The sprayable diluted herbicidal formulations according to the invention give optimum drift control and droplet deposition, and have also high storage stability and do not tend to block the spray nozzles.

In some embodiments, the invention is an aqueous adjuvant concentrate comprising, dissolved therein: a. from 15 to 45% by weight of a potassium salt chosen among di-potassium phosphate, potassium sulfate, potassium nitrate, tri-potassium citrate, potassium salts of ethylenediaminetetraacetic acid (EDTA) and mixture thereof; b. from 0.5 to 6% by weight of at least a surfactant and c. from 3 to 9% by weight of a hydroxylpropyl tamarind gum (HPT).

In another embodiment, the aqueous adjuvant is a concentrate as described herein, comprising: a. from 20 to 35% by weight of a potassium salt chosen among di-potassium phosphate, potassium sulfate, potassium nitrate, tri-potassium citrate, potassium salts of EDTA and mixture thereof; b. from 1 to 4% by weight of at least a surfactant and c. from 3 to 8% by weight of a HPT.

In still another embodiment, the invention is an aqueous adjuvant concentrate as described herein wherein said potassium salt is a mixture of di-potassium phosphate, potassium nitrate and tri-potassium citrate.

In yet another embodiment, the invention is an aqueous adjuvant concentrate as described herein, wherein said surfactant is an anionic surfactant.

In one embodiment, the aqueous adjuvant concentrate is one as described herein, wherein said anionic surfactant is chosen among alkyl sulfosuccinic acids and anionic esters of alkylpolyglycosides.

In another embodiment, the aqueous adjuvant concentrate is one as described herein, wherein the hydroxypropyl tamarind gum has a hydroxypropyl molar substitution of from 0.1 to 2.5.

In still another embodiment, the aqueous adjuvant concentrate is one as described herein, wherein said hydroxypropyl tamarind gum has a hydroxypropyl molar substitution of from 0.2 to 1.0.

In one embodiment, the invention is a sprayable herbicidal formulation comprising from 0.01 to 5% by weight of at least one herbicide and the aqueous adjuvant concentrate of claim 1) in such an amount that the concentration of HPT in the formulation is comprised between 0.01 and 0.4% by weight.

In yet another embodiment, the sprayable herbicidal formulation as described herein, is one wherein said herbicide is chosen among N-(phosphonomethyl) glycine (Glyphosate) and its salts, Dicamba and its salts, 2-4D and its salts, and mixture thereof.

In still another embodiment, the sprayable herbicidal formulation as described herein, is one wherein said herbicide is a mixture of N-(phosphonomethyl) glycine and Dicamba, or salts thereof.

The following Examples serve to illustrate the stability of aqueous adjuvant concentrate according to the invention.

EXAMPLES

Example 1-16

Different amounts of potassium salts (see Tables 1-3) were dissolved in deionized water at room temperature under stirring.

After complete solubilization, SAG® 1572, an antifoaming agent available from Momentive Inc., and Emulson AGE/EC/UP, an alkyl polyglucoside citrate, both commercialized by Lamberti S.p.A., were added.

The mixture was maintained under mechanical stirring until complete dissolution, then hydroxypropyl tamarind gum was added. Two hydroxypropyl tamarind gums were tested: HPT1, MS 0.58 and Brookfield® RV viscosity of 2,400 mPa·s at 5% wt water sol., 20° C. and 20 rpm, and HPT2, MS 0.42 and Brookfield® RV viscosity of 6,840 mPa·s at 5% wt water sol., 20° C. and 20 rpm.

Comparative Examples were prepared by substituting the HPT with two hydroxypropyl guar: HPG1, having a MS of 0.25 and a Brookfield® RV viscosity of 60,600 mPa·s at 10% wt water sol., 20° C. and 20 rpm and HPG2, having a MS of 0.29 and a Brookfield® RV viscosity of 22,700 mPa·s at 2% wt water sol., 20° C. and 20 rpm.

The pH of some of the solutions was corrected to about 7.5 by adding a 50% wt solution of citric acid.

A 10% wt of Attagel 50, Attapulgite available from BASF AG, was added to the adjuvant concentrates of Examples 14-16. The 10% wt stock solution was prepared by pre-dispersing 10 g of Attagel 50 in 30 g of propylene glycol, adding 60 g of water and stirring with a mechanical blade stirrer set at about 3000 rpm. The stirring was continued until the viscosity reached a steady state indicating full activation of the attapulgite.

Tables 1-3 show the amount in grams of the ingredients utilized and the appearance, the cold stability (0° C. for 7 days) and the Brookfield® RV viscosity in mPa·s, determined at 25° C. and 20 rpm, of the final solutions.

Tables 1-3 also reports the appearance of the aqueous adjuvant concentrate after a cycle of freeze & thaw, which was conducted running 3 different cycles of freeze at 0° C. for 24 hours, followed by thaw at 54° C. for other 24 hours.

TABLE 1

| Ingredient | Ex. 1 | Ex. 2* | Ex. 3 | Ex. 4* | Ex. 5 | Ex. 6 | Ex. 7* |
|---|---|---|---|---|---|---|---|
| Deionized Water | To 100 | To 100 | To 100 | To 100 | To 100 | To 100 | To 100 |
| $K_2HPO_4$ | 26 | 26 | 26 | — | — | — | — |
| $KNO_3$ | — | — | — | 10 | 20 | 40 | 20 |
| Citric acid (50%) | 11 | 11 | 11 | — | — | — | — |
| SAG 1572 | 0.05 | 0.05 | 0.05 | 0.05 | 0.05 | 0.05 | 0.05 |
| EMULSON AGE/EC/UP | 1.5 | 1.5 | 3 | 1.5 | 1.5 | 1.5 | 3 |
| HPT1 | 7 | 10 | — | 2 | 6 | 5 | — |
| HPT2 | — | — | 7 | — | — | — | — |
| HPG1 | — | — | — | — | — | — | 7 |
| Appearance | Stable | Paste | Stable | Phase Sep. | Stable | Stable | Paste |
| Cold Stability | Stable | Paste | Stable | Phase Sep. | Stable | Stable | Paste |
| Freeze & Thaw | Stable | Paste | Stable | Phase Sep. | Stable | Stable | Paste |
| RVT Viscosity | 7500 | 16800 | 8000 | 2100 | 6800 | 7500 | 18300 |

*comparative
N.D. = not determined
Phase Separ. = phase separation occurred

TABLE 2

| Ingredient | Example 8* | Example 9 | Example 10* | Example 11* |
|---|---|---|---|---|
| Deionized Water | To 100 | To 100 | To 100 | To 100 |
| K3 Citrate | 15 | 20 | 30 | 30 |
| SAG 1572 | 0.05 | 0.05 | 0.05 | 0.05 |
| EMULSON AGE/EC/UP | 1.5 | 1.5 | 1.5 | 1.5 |
| HPT1 | 2 | 5 | 10 | — |
| HPG1 | — | — | — | 7 |
| Appearance | Phase Sep. | Stable | Gel | paste |
| Stability | Phase Sep. | Stable | Gel | paste |
| Freeze & Thaw | Phase Sep. | Stable | Gel | paste |
| RVT Viscosity | 2200 | 5100 | N.D. | 22500 |

*comparative
N.D. = not determined
Phase Separ. = phase separation occurred

TABLE 3

| Ingredient | Example 12 | Example 13* | Example 14 | Example 15 | Example 16* |
|---|---|---|---|---|---|
| Deionized Water | To 100 | To 100 | To 100 | To 100 | To 100 |
| K2HPO4 1 | 18 | 18 | 15 | 15 | 15 |
| KNO3 | 6.1 | 6.1 | 5 | 5 | 5 |
| K3 Citrate | 6.1 | 6.1 | 5 | 5 | 5 |
| Citric acid (50%) | 6.6 | 6.6 | 5 | 5 | 5 |
| SAG 1572 | 0.05 | 0.05 | 0.05 | 0.05 | 0.05 |
| EMULSON AGE/EC/UP | 1.5 | 1.5 | 1.5 | 1.5 | 1.5 |
| ATTAGEL 50 | — | — | 0.1 | 0.2 | 0.1 |
| HPT1 | 6.5 | 2.5 | 5 | 5 | — |
| HPG2 | — | — | — | — | 3.5 |
| Appearance | Stable | Phase Sep. | Stable | Stable | Gel |
| Cold Stability | Stable | Phase Sep. | Stable | Stable | Gel |
| Freeze & Thaw | Stable | Phase Sep. | Stable | Stable | Gel |
| RVT Viscosity | 6700 | 1200 | 2200 | 2800 | N.D. |

*comparative
N.D. = not determined
Phase Separ. = phase separation occurred

The aqueous adjuvant concentrates (dispersions) are considered stable when no phase separation or precipitation or gelification occur.

Spray Drift Test

The antidrift properties of the aqueous adjuvants of the invention were evaluated by determining the droplet sizes of the sprays of diluted herbicide formulations prepared with the concentrates of the Examples described above.

A Sympatec Helos/Vario KR particle size analyzer was used. This system uses laser diffraction to determine particle size distribution in a range from 18 to 3500 microns. All testing was performed in a low speed wind tunnel at 15 mph. Table 4 summarize the testing parameters.

TABLE 4

| Parameter | Value |
|---|---|
| Wind speed | 24.1 km/h |
| Temperature | 21.4° C. |
| Relative humidity | 66% |
| Nozzle | AIXR11003 |
| Pressure | 276 kiloPascal (40 psi) |
| Measurement distance | 304 mm |
| Particle size analyzer | HELOS KR with R7 lens |

The width of the nozzle plume was analyzed by moving the nozzle across the laser by means of a linear actuator. The tests were replicated at least three times for each diluted sprayable herbicide formulation.

Sprayable herbicide formulations were prepared using Roundup PowerMax® (glyphosate based herbicide, available from Monsanto) at a concentration of 2% v/v in water and adding the amount of aqueous adjuvant concentrates reported in Table 5. Water and a formulation containing only the herbicide were used as reference. The results are reported in Table 5.

The percent less than 150 μm (Pct <150 μm) is the percentage of the spray volume that is 150 μm and smaller, with percent less 210 μm (Pct <210 μm), and 730 μm (Pct <730 μm) being similar measurements.

TABLE 5

| | | Pct | | |
|---|---|---|---|---|
| | % v/v | <150 μm | <210 μm | <730 μm |
| Water | — | 3.02 | 7.78 | 90.95 |
| Roundup Power Max | — | 6.57 | 14.3 | 92.2 |
| Example 1 | 1 | 4.35 | 10.22 | 88.23 |
| Example 3 | 1 | 4.61 | 10.71 | 88.83 |
| Example 5 | 1 | 4.32 | 10.01 | 89.24 |
| Example 9 | 1 | 4.67 | 10.55 | 89.78 |
| Example 12 | 1 | 4.4 | 10.38 | 89.33 |
| Example 14 | 1.5 | 4.26 | 9.88 | 88.12 |
| Example 15 | 0.6 | 3.2 | 8.65 | 89.06 |

The addition of the aqueous adjuvant concentrates of the invention result in coarser spray with a lower percentage of small droplets i.e. those having a diameter below 150 microns, which are more prone to drift. At the same time it produces a lower percentage of very large droplets, i.e. those having a diameter above 730 microns, which show a lower herbicidal efficacy. This test demonstrates the optimal spray drift properties of the aqueous adjuvant concentrates of the invention.

What is claimed is:

1. An aqueous adjuvant concentrate comprising:

a. from about 15 to about 45% by weight of a potassium salt chosen among di-potassium phosphate, potassium sulfate, potassium nitrate, tri-potassium citrate, potassium salts of ethylenediaminetetraacetic acid and mixture thereof;

b. from about 0.5 to about 6% by weight of at least one surfactant and c. from about 3 to about 9% by weight of a hydroxypropyl tamarind gum;

wherein a, b, and c are dissolved into the aqueous adjuvant.

2. The aqueous adjuvant concentrate of claim 1 wherein:

a. is from about 20 to about 35% by weight of a potassium salt chosen among di-potassium phosphate, potassium sulfate, potassium nitrate, tri-potassium citrate, potassium salts of ethylenediaminetetraacetic acid, and mixture thereof;

b. from about 1 to about 4% by weight of at least a surfactant and c. from about 3 to about 8% by weight of a tamarind gum.

3. The aqueous adjuvant concentrate of claim 1 wherein the potassium salt is a mixture of di-potassium phosphate, potassium nitrate and tri-potassium citrate.

4. The aqueous adjuvant concentrate of claim 1 wherein the surfactant is an anionic surfactant.

5. The aqueous adjuvant concentrate of claim 4 wherein the anionic surfactant is chosen among alkyl sulfosuccinic acids and anionic esters of alkylpolyglycosides.

6. The aqueous adjuvant concentrate of claim 1 wherein the hydroxypropyl tamarind gum has a hydroxypropyl molar substitution of from about 0.1 to about 2.5.

7. The aqueous adjuvant concentrate of claim 6 wherein the hydroxypropyl tamarind gum has a hydroxypropyl molar substitution of from about 0.2 to about 1.0.

* * * * *